(12) United States Patent
van de Laar et al.

(10) Patent No.: US 7,560,249 B2
(45) Date of Patent: Jul. 14, 2009

(54) METHOD FOR THE PRODUCTION OF A HETEROLOGOUS PROTEIN BY A FUNGUS

(75) Inventors: Antonius Johannes van de Laar, Vlaardingen (NL); Nigel Malcolm Lindner, Bedford (GB); Peter Nieuwpoort, Vlaardingen (NL)

(73) Assignee: Unilever Bestfoods, North America, division of Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 10/450,211

(22) PCT Filed: Nov. 16, 2001

(86) PCT No.: PCT/EP01/13457

§ 371 (c)(1),
(2), (4) Date: Nov. 10, 2003

(87) PCT Pub. No.: WO02/48382

PCT Pub. Date: Jun. 20, 2002

(65) Prior Publication Data

US 2004/0077069 A1    Apr. 22, 2004

(30) Foreign Application Priority Data

Dec. 13, 2000   (EP) ................... 00311095

(51) Int. Cl.
*C12P 21/06*  (2006.01)
*C12P 1/00*   (2006.01)
*C12P 39/00*  (2006.01)
*A61K 39/38*  (2006.01)
*A61K 39/00*  (2006.01)
*A61K 38/00*  (2006.01)

(52) U.S. Cl. ............... 435/69.7; 435/68.1; 435/69.1; 435/41; 435/42; 424/184.1; 424/185.1; 530/300

(58) Field of Classification Search ............. 435/320.1, 435/69.7, 70.1
See application file for complete search history.

(56) References Cited

FOREIGN PATENT DOCUMENTS

| EP | 0 481 008 B1 | * 11/1997 |
|----|--------------|-----------|
| EP | 481008       | 11/1997   |
| EP | 1134231      | 9/2001    |
| WO | 97/02343     | 1/1997    |

OTHER PUBLICATIONS

Shiba et al, Journal of Bioscience and Bioengineering, vol. 89, No. 5, p. 429-430.*
Jin et al, Journal of Biotechnology, 54, 1997, 161-174.*
Jin et al (Journal of Biotechnology, 54, 1997, 161-174).*
Shiba et al (Journal of Bioscience and Bioengineering, vol. 89, No. 5, p. 429-430).*
International Search Report on PCT/EP 01/13457 dated Oct. 9, 2002.
H. Schlegel in *General Microbiology*, Cambridge University Press, 1992, 7th Edition, p. 194.
Shiba et al., *Journal of Bioscience and Bioengineering*, vol. 89, pp. 426-430, 2000.
Saliola, M. et al. *Applied and Environmental Microbiology*, Jan. 1999, p. 53-60.
Griffith et al., *Biotechnology Advances*, vol. 13, No. 3, pp. 375-402 (1995).
Jin Sha et al. *Journal of Biotechnology*, vol. 54, No. 3, 1997, pp. 161-174.

* cited by examiner

*Primary Examiner*—Robert Mondesi
*Assistant Examiner*—Vanessa L. Ford
(74) *Attorney, Agent, or Firm*—Gerard J. McGowan, Jr.

(57) ABSTRACT

Production of heterologous protein by fungal cells is good when the feeding medium comprises a carbon source comprising 50 to 100 wt % of ethanol and an inducer.

12 Claims, No Drawings

METHOD FOR THE PRODUCTION OF A HETEROLOGOUS PROTEIN BY A FUNGUS

FIELD OF THE INVENTION

The invention relates to a method for the production of a heterologous protein or peptide in a fungus.

BACKGROUND OF THE INVENTION

Heterologous protein production in a host such as a fungus is well known. EP-A-481,008 discloses production of a heterologous protein in a yeast, which is grown on glucose.

The industrial, large scale production of a heterologous protein by a host organism in a fed batch fermentation generally shows three phases.

The first phase is the batch phase which is defined as the phase wherein the cells are grown to the required concentration. In this phase the cells are grown exponentially. Models describing the batch phase assume that cells do not die, that oxygen is present in excess, and that all other conditions are such that growth can occur unlimited. This implies that in the batch phase all nutrient requirements are supplied in sufficient quantity. In summary the batch phase is the phase where cells are amplified while (heterologous) protein production is still low.

The second phase is the feed phase which is defined as the phase wherein carbon source and other requirements are fed to a fermenter in a relatively concentrated liquid stream at a precalculated rate, the "feed rate". In this phase emphasis is on protein production by the grown cells and cell growth leading to an increase of biomass. Substrate that is fed to the fermenter is at this stage used generally for cell growth and product synthesis. The cell growth is controlled by the feed rate to obtain an optimum in cell growth and production of eterologous protein.

Eventually the third phase is reached which is defined as the decline phase, wherein limiting conditions arise. In this phase for example oxygen concentration in the fermenter is low to zero, leading in some cases to formation of ethanol. In this stage, most cells will focus on maintenance and usually product synthesis is reduced. Although cell growth may still be observed in this phase, growth is generally very limited to zero. Gradually cells may loose viability in this phase.

The production of heterologous protein on a medium comprising a common carbon source like glucose or another sugar based carbon source is satisfying until limiting conditions start to exist at the end of the feed phase. Examples of limiting conditions include reduced oxygen concentration, reduced nutrients like vitamins, carbon, nitrogen, and accumulation of toxic compounds in the growth medium.

If a fungus, especially a yeast, is grown on a medium comprising glucose as carbon source, as soon as limiting conditions arise, heterologous protein production is considerably reduced.

For yeasts grown on common medium including a sugar as carbon source the above-described phases exist in a fed-batch fermentation. Hence once the decline phase has started, specific production, which is defined as amount of heterologous protein or peptide produced per gram of biomass, is maintained or reduced. Even although cell density is high, product synthesis is hence low in the decline phase.

Another disadvantage of common media which often comprise glucose as a carbon source, is the high amount of substrate that is converted to biomass instead of conversion to product which is usually a heterologous protein in the context of this invention. Hence in such systems, a relatively high amount of biomass unavoidably accompanies the production of high levels of heterologous protein.

This high biomass leads to a viscous fermentation medium in which for example oxygen limitation easily arises.

Therefore there is a desire for a method for heterologous protein production in a host like a fungus which leads to high heterologous protein yield even under limiting conditions, where normally decline and reduced specific production would exist, whereas at the same time the specific production of the growth system is maintained or increased compared to the known growth systems.

The method of the current invention overcomes at least one of the indicated problems.

SUMMARY OF THE INVENTION

It has surprisingly been found that fungi grown on a medium comprising ethanol as the main carbon source and an inducer like galactose to control the production of a heterologous protein, show high specific production of heterologous protein, while specific production of the heterologous protein is surprisingly high even under limiting conditions.

Surprisingly fungi grown according to this method do not show the well known characteristics of decline which are encountered for fungi grown on the traditional glucose based media. Under continuation of the feed with medium comprising this specific carbon source, the fungi maintain or even increase the absolute and specific production level of heterologous protein.

Therefore the invention relates to a method for the production of a heterologous protein by a fungus comprising growth of said fungus on a medium comprising a carbon source wherein 50-100 wt % of said carbon source is ethanol, and wherein the medium additionally comprises an inducer.

DETAILED DESCRIPTION OF THE INVENTION

In the context of the invention, the term fungus encompasses yeasts and moulds.

For the purpose of the invention, the term heterologous protein is meant to include both proteins and peptides.

A heterologous protein is a protein which is not naturally produced by the fungus but only after the fungus has been modified to this extent.

Where weight percentages are indicated these are weight percentages on total product or total medium weight, unless otherwise is indicated.

Where the term oxygen concentration is used, reference is made to dissolved oxygen concentration which is measured by the method illustrated in the examples.

The end of the batch phase is defined as the moment when all carbon substrate provided to the cells has been consumed.

Induction phase is defined as the phase which starts after the batch phase from the moment when induction of heterologous protein is started until the moment that maximum induction is obtained for the specific inducer concentration used.

Carbon source is defined as the substrate which provides the supply of carbon and energy to the cell. Fungi obtain their cell carbon predominantly from organic compounds. These commonly serve as both carbon source and energy source: they are partially assimilated into the cell material and partially oxidized to provide energy. In this context reference is made to H. Schlegel in General microbiology, Cambridge University press, 1992, $7^{th}$ edition, page 194.

The invention relates to a method for the production of a heterologous protein by a fungus. In order to produce this protein, the fungus is genetically modified such that controlled production of this heterologous protein or peptide is possible.

Any suitable construct or transformation method can be used for this genetic modification. Examples of suitable constructs and transformation methods are given in EP-A-481,008 which is herewith incorporated by reference.

In general the modified fungus will after modification comprise a (integrated) vector which comprises the gene encoding the heterologous protein, under the control of a promoter. The activity of the promoter is regulated by a so called inducer. Examples of promoters include the galactose promoters like GAL4, GAL7 which are induced by galactose; methanol induced promoters, induced by methanol; ethanol promoters, induced by ethanol; temperature regulated promoters, induced by a temperature change; phosphate regulated promoters, induced by the presence of phosphate; and glucose repressible promoters, induced by the absence of glucose.

The fungus is grown on a medium comprising a carbon source of which 50 to 100 wt % is ethanol, in combination with the presence of an inducer in the medium.

In the art, the use of ethanol as a carbon source is generally discouraged as is exemplified by the disclosure cited below. In summary use of ethanol instead of glucose as carbon source is reported to reduce the biomass yield, to require higher oxygen consumption and hence providing no or limited growth under oxygen limiting conditions. Furthermore ethanol toxicity of strains may lead to loss in viability and cell death. This is for example disclosed in table 1 of The yeasts, vol 3 $2^{nd}$ ed chapter 6. Special reference is made to appendix 1 of this disclosure which discloses that for yeast, the growth rate on ethanol is 0.1 $h^{-1}$ vs. 0.35 $h^{-1}$ on glucose. This appendix furthermore discloses that on a medium with ethanol as carbon substrate, yeasts show a higher oxygen consumption than on a medium comprising glucose as carbon substrate.

Growth of cells on ethanol as a carbon source is further described by Shiba et al (J. of bioscience and bioengineering, vol 89, page 426-430, 2000). Shiba disclose expression of carboxypeptidease Y (CPY) using GAL10 promoter in a *Saccharomyces cerevisiae* gal80 mutant. The growth medium comprises ethanol as the sole carbon source. Upon start of ethanol feed, both the growth rate and CPY production are reported to decrease. This system is not under control of an inducer.

The current invention provides a process wherein protein production is maintained or even increased in the presence of a medium comprising a carbon source of which 50 to 100 wt % is ethanol, especially when limiting growth conditions arise. Furthermore the process according to the invention is applicable for any type of fungus and does not require specific gal80 mutants for growth. The process of the invention is as well controllable via induction.

Saliola, M et al (applied and environmental microbiology, January 1999, p. 53-60) discloses use of the ethanol-inducible KlADH4 promoter for heterologous gene expression in *Kluyveromyces lactis*. This document teaches that expression is optimal when ethanol is used as promoter and simultaneously as sole carbon source in a fed batch system. This production system does not enable control of gene expression in the feed phase.

A further benefit of the process according to the invention, is control of heat production which is important for production of heat labile proteins.

It is preferred that the medium comprises a carbon source of which 50 to 100 wt % is ethanol, in combination with the presence of an inducer in the medium, throughout all phases, but is was found that it is possible to use a medium which does not fulfill these requirements in the batch phase, as long as the requirements are fulfilled by the feed phase medium.

In a preferred embodiment, the invention relates to a method for the production of a heterologous protein by a fungus, which method comprises a batch phase and a feed phase and wherein the feed phase medium comprises a carbon source of which 50 to 100 wt % is ethanol and wherein the feed phase medium additionally comprise an inducer.

Compared to the known growth systems, which usually contain glucose or another sugar as the main carbon source, the medium according to the invention enables high specific production levels even under limiting conditions; i.e. there is preferably no decline phase.

The specific production was even found to be highest in the feed phase under limiting oxygen conditions, whereas for glucose based growth systems, the highest specific production is usually found in the feed phase, where biomass amount is still relatively low.

Without wishing to be bound by any theories, applicants believe that the decline phase is extended or even absent due to the use of a medium comprising a carbon source of which 50 to 100 wt % is ethanol, in the method of the invention.

In the process of producing a heterologous protein, the feed conditions are preferably optimised such that cell growth rate and heterologous protein production are optimal.

As indicated above, if the fungus is grown on industrial scale, a fed batch system using a fermenter is highly preferred.

In another preferred embodiment, the invention relates to a method for the production of a heterologous protein by a fungus which method comprises a batch phase, an induction phase and a feed phase wherein in said feed phase a) fungal cells are grown to a cell density of at least 5 g/l on a medium comprising any carbon source, without specific preference, and subsequently the fungal cells are grown to a cell density of more than 5 g/l, preferably 10 to 90 g/l, more preferred 40 to 60 g/l, using a medium comprising an inducer and a carbon source wherein 50-100 wt % of said carbon source is ethanol b) after the cell density of step (a) has been obtained, limiting growth conditions are created, c) after these limiting conditions have set in, the cells are further grown on a medium comprising a carbon source wherein 50-100 wt % of said carbon source is ethanol.

In this preferred method in a first step cells are grown in a batch phase until carbon substrate has been consumed, and in a second step the cells are grown to a sufficient cell density to enable heterologous protein production in high amounts. In the first stages of this second phase, heterologous protein production is induced by addition of an inducer to the feed medium. The time it takes to come from zero induction, and thus very low level of heterologous protein production, until induction is maximal, is called the induction phase. This induction phase constitutes the first stage of the feed phase.

Limiting conditions in a fermenter can be obtained in several ways. Limiting conditions are defined as those conditions wherein exponential cell growth is no longer possible and cell growth is decreasing.

Preferably in the method of the invention, limiting conditions in a medium are created by a method selected from the group comprising a) reduction of the oxygen concentration in The fermenter medium; (e.g. from 0 to below 30%) preferably to below 30%, more preferred below 15%, b) overfeeding the medium with ethanol until the ethanol level in the medium is at or above the growth limiting concentration for the cells of the strain that is grown in the medium c) decreasing the level of other essential ingredients for growth of the cells, said ingredient preferably being selected from nitrogen, phosphor, sulphur and vitamins.

Preferably after the batch phase the feed profile is exponentially increasing with biomass production. When oxygen limitation arises and the decline phase is entered, the feed rate is preferably set to a rate as to maintain an ethanol concentration of below 10 vol % in the fermenter medium. This can for example be obtained by a linear feed rate or a pulsed feed rate or a step wise feed rate.

In an even more preferred embodiment, the method of the invention is carried out as a repeated fed batch process.

Preferably the inducer is suitable for turning on the promoter which is operably connected to the heterologous gene in the gene construct used for transformation of the host fungus. Preferred inducers are galactose, methanol, temperature, and phosphates.

The most preferred inducer is galactose.

The current invention does not relate to expression methods wherein ethanol is both used as an inducer and as (part of) the carbon source.

When galactose is the inducer, the amount of galactose in the medium should preferably be such that the promoter is turned on to the desired level while the amount is so low, that galactose is not metabolised. To prevent this, it is possible to use a strain which is unable to metabolise the inducer.

Preferably the composition of the feed medium is such that the medium in the fermenter comprises from 0.1 to 10 wt % galactose, more preferred from 0.05 to 1 wt %, even more preferred from 0.05 to 0.2 wt % galactose.

The carbon source in the medium according to the invention comprises at least 50 wt % and up to 100 wt % ethanol. Preferably the carbon source comprises from 80 to 100 wt % ethanol. The remainder of the carbon source can for example be a sugar such as glucose, galactose, lactose, sucrose, fructose or another compound like glycerol, acetate, or complex carbon substrates like whey and molasses.

The fungus can be a yeast or a mould. Examples of suitable yeast genera include *Saccharomyces, Kluyveromyces, Pichia, Hansenula*. Examples of suitable moulds include *Aspergillus, Rhizopus, Trichoderma*.

The especially preferred organism is *Saccharomyces cerevisiae*.

The heterologous protein can be any protein or peptide of which production is desired. The method according to the invention was found to be especially suitable for production of antifreeze peptides, antibodies or fragments thereof, or enzymes such as cutinase and galactosidase.

Antifreeze peptides are proteins that have the ability to modify the growth of ice, and are for example described in biotechnology advances vol. 13, no 3, pp 375-402, 1995 by Griffith et al, which is herewith incorporated by reference.

The medium for the various phases in the growth of the fungus generally comprise a carbon source, optionally an inducer, who's presence is required after the batch phase, and optionally further ingredients such as vitamins, yeast extract, trace metal ions, acidification agents to keep the pH at a desired level, phosphate salts, sulphate salts water, and antifoaming agent.

According to another preferred embodiment the invention relates to a method for producing a heterologous protein or peptide wherein the batch medium comprises from 1-40 wt % glucose, water, trace metals, optionally an antifoaming agent, yeast extract, vitamins, phosphate salts and sulphate salts and wherein the feed medium comprises from 5 to 35 vol % ethanol, 0.1-10 wt % galactose, water, trace metals, and optionally antifoaming agent, yeast extract, vitamins, phosphate salts and sulphate salts and wherein the "feed rate" "φ" is from 0.25 to 4 g/min on 10 litre scale or a corresponding value for a larger scale fermentation.

The invention furthermore relates to a heterologous protein isolate, especially antifreeze peptide isolate, obtained by the method according to the invention.

The invention will now be illustrated by the following non-limiting examples.

EXAMPLES

Media and Cultivation

All media and cultivation data is based on 10 litre scale ethanol fermentation.

For 10 m³ scale it's roughly the same adapted to scale factor 1000.

Media

Preculture Media:

| INOCULUM MEDIA | Compound | g/l | Supplier |
|---|---|---|---|
| YNB | YNB w/o amino acids | 6.7 | Difco |
| Yeast nitrogen base | Glucose*1aq | 5 | AVEBE |
| | In demineralised water | | |
| YPD | YE | 10 | Difco |
| Yeast peptone dextrose | bacto pepton | 20 | Difco |
| | Glucose*1aq | 20 | AVEBE |
| | In demineralised water | | |

Batch and feed media are listed in table 1 for 10 litre scale

TABLE 1

| | | Concentration (g/kg) | | |
|---|---|---|---|---|
| Compound | Supplier | Batch | Feed Ethanol | Feed Comp. Example Glucose |
| Glucose | Avebe | 22.0 | — | 440.0 |
| Tap water | | | | |
| EtOH* | Lamers & Pleuger | — | 333.84 | — |
| Tap water | | | | |
| Galactose | HMS | — | 3.0 | 3.0 |
| Tap water | | | | |
| YE Kat G | Ohly | 10.0 | 25.0 | 25.0 |
| KH$_2$PO$_4$ | Acros | 2.1 | 12.0 | 12.0 |
| MgSO$_4$•7H$_2$O | Merck | 0.6 | 2.5 | 2.5 |
| Egli vitamins | See Table 2 | 1.0 | 2.0 | 2.0 |
| Egli trace metals | See Table 2 | 10.0 | 20.0 | 20.0 |
| Structol J 673 | Schill & Seilacher | 0.4 | 0.8 | 0.8 |
| Tap water | | | | |
| Total weight (g) | | 5,500 | 4,000 | 4,000 |

*Ethanol pure, 96.2% v/v content, non denatured
All media were sterilised 25 minutes at 121° C./1.2 bar (Linden autoclave), sugars separately. The tap water amounts are described below and total amount is such that total weight is indicated in the bottom row of table 1.

described below and total amount is such that total weight is as indicated in the bottom row of table 1.

Egli Vitamins and Trace Metals Composition

TABLE 2

| Egli vitamins (1000 × stock solution) | | Egli trace metals (100 × stock solution) | |
|---|---|---|---|
| Compound | g/l | Compound | g/l |
| Thiamine (HCl) | 5.00 | $CaCl_2 \cdot 2H_2O$ | 5.50 |
| Meso-inosit | 47.00 | $FeSO_4 \cdot 7H_2O$ | 3.73 |
| Pyridoxine | 1.20 | $MnSO_4 \cdot 1H_2O$ | 1.40 |
| Panthotenic | 23.00 | $ZnSO_4 \cdot 7H_2O$ | 1.35 |
| Biotine | 0.05 | $CuSO_4 \cdot 5H_2O$ | 0.40 |
| | | $CoCl_2 \cdot 6H_2O$ | 0.45 |

Vitamins were 0.22 μm filter sterilized

Strain

The strain used was *Saccharomyces cerevisiae* CEN.PK102-3A. The basic CEN.PK2 *S. cerevisiae* strain is commercially available from EUROSCARF, Institute for Microbiology, Johann Wolfgang Goethe-University Frankfurt, Marie-Curie-Strasse 9; Building N250, D-60439 Frankfurt, Germany.

This *S. cerevisiae* strain is not able to metabolise galactose as the GAL1 gene has been disrupted by insertion of sequences derived form the *S. cerevisiae* URA3 gene. The host strain was transformed with an expression plasmid comprising the following elements:

Promoter: GAL7 promoter, leader GAPDH. GAL7 promoter: two upstream activating sequences are always present. They are 2 natural elements that are part of the sequence as attached.

Selection marker: Leu2d

Signal sequence: invertase (SUC2)

Integration target: fragment of rDNA repeat with unique restriction site for targeting integration to a specific region in yeast chromosome XII.

Heterologous gene:

Example 1

An Antifreeze Protein Gene Encoding the Ocean Pout HPLC12 Antifreeze Protein (WO-A-9702343)

Example 2

K609B, an Antibody Against Virulence Factors in Piglets

Example 3

Protein VHH G which is HGL11, which is a Heavy Chain Immunoglobulin; the Lipase Inhibitor Against Human Gastric Lipase Disclosed in EP-A-1,134,231

Example 4

Protein VHH P which is HPL18, which is a Heavy Chain Immunoglobulin; the Lipase Inhibitor Against Human Pancreas Lipase Disclosed in EP-A-1,134,231.

The proteins of example 2-4 are antibodies obtained by immunisation of a llama according to the procedures disclosed in EP-A-1,134,231.

Cultivation

Strain Storage

Strains were stored at −80° C. in single batch from YNB-grown cultures diluted 1:1 with a mixture of skimmed milk and 20% glycerol.

Inoculation 50 ml YNB was inoculated with 1 ml stored strain, and incubated for 48 hours ±2 hours at 30° C. at 150 r.p.m.

Subsequently the inoculum was transferred to 500 ml of 2% YPD, followed by incubation for 24 hours ±2 hours at 30° C. at 150 r.p.m.

Fermenter

The fermentations were performed in standard fermenters with a working volume of ten litres. For temperature control, the fermenter was equipped with a cooling coil and a heating finger. Baffles were of standard dimensions. A Rushton type impeller with six blades was used for stirring. Dissolved oxygen ($DO_2$) was measured with an Ingold® $DO_2$-electrode (Mettler-Toledo) and the pH was measured with an Ingold® Impro 3000 gel electrode (Mettler-Toledo). A mass spectrophotometer Prima 600 (VG gas analysis systems) was used for measuring the offgas. The whole fermentation process was automated and software-controlled but could as well be carried out manually on the basis of the guidance provided below.

A feed profile was imposed to control the fermentation. pH was controlled using 3M phosphoric acid (Baker) and 12.5% v/v ammonia (Merck).

$DO_2$ was controlled at 30% by automatic adjustment of the impeller speed until maximum stirrer speed occurred (1000 rpm).

During fermentation 5 ml samples were taken and cooled at 4° C. with an autosampler for dry weight determination and product concentration analysis.

Batch Phase

To start the batch phase 500 mL of YPD inoculum was added to 5.5 L batch medium. Fermentation parameters were as according to table 3.1 When the ethanol content in the offgas decreases to 300 ppm the exponential feed was started.

Feed Phase

The feed medium was separated into two feed bottles connected to the same pump.

One feed bottle contained the ethanol and tap water to 2 Litres and was fed to the fermenter through the bottom plate.

Second feed bottle contained all other feed components and water to 2 Litres and was fed through the top plate.

From both bottles, connected to one pump, the same exponential feed rate was applied according to equation 1. For two bottles the resulting feed rate is twice the pumprate.

$$\Phi_{v,t} = \frac{\mu * X_0 * e^{\mu * t}}{\rho_{feed} * Y_{X,S} * 60} \text{ [g/min]} \quad \text{(equation 1)}$$

| | |
|---|---|
| $\Phi_{v,t}$ = feed rate | g/min |
| $\mu$ = growth rate | $h^{-1}$ |
| $X_0$ = biomass at feedstart | g (Mw = 24.6 g/mol) |
| t = time since feedstart | min |
| $\rho_{feed}$ = feed density | g ethanol/g feed |
| $Y_{x,s}$ = estim. yield of biomass | g X/g substrate |
| 60 = time factor | min/h |

Feed parameters were according to table 3.

TABLE 3

Fermentation feed parameters for 10 liters ethanol fermentation

| Parameter | Value |
|---|---|
| $\mu$ (l/h) | 0.06 |
| $X_0$ (mol) | 1.06 |
| $\rho_{feed}$ (g/g) | 0.41 |
| $Y_{xs}$ (g/g) | 0.45 |
| T batch (° C.) | 30 |
| T feed (° C.) | 21 |
| Airflow batch (l/min) | 2 |
| Airflow feed (l/min) | 6 |
| $DO_2$ (%) | 30 |
| $DO_2$ minimum (%) | 0 |
| PH | 5 |
| SS min (rpm) | 300 |
| SS max (rpm) | 1000 |
| EtOH criterium feedstart (ppm) | 300 |
| EtOH criterium declinestart (ppm) | 800 |
| EtOH maximum (ppm) | 2000 |
| Initial total feed rate (g/min) | 0.28 g/min |
| Linear total feed rate (g/min) | 2 g/min |

When the oxygen concentration was 0%, the limiting conditions were set in and the pumprate was set to linear feed rate. This feeding was continued until all feed was depleted.

Results

Example 1

Ethanol as carbon source

| Time (hr) | AFP (mg/kg fermentation broth) | Dry matter (g/kg) | Specific production* (mg/g) |
|---|---|---|---|
| 0 | 0 | 2.4 | 0 |
| 3 | 0 | 3.4 | 0 |
| 6 | 0 | 5.7 | 0 |
| 9 | 0 | 7.6 | 0 |
| 12 | 0 | 10.9 | 0 |
| 15 | 0 | 10.5 | 0 |
| 18 | 0 | 11.7 | 0 |
| 21 | 0 | 13.3 | 0 |
| 24 | 0 | 15.6 | 0 |
| 27 | 7.0 | 17.9 | 0.393 |
| 30 | 11.4 | 20.7 | 0.549 |
| 33 | 17.9 | 24.8 | 0.721 |
| 36 | 24.2 | 28.8 | 0.840 |
| 39 | 32.4 | 32.7 | 0.990 |
| 42 | 41.8 | 38.4 | 1.089 |
| 45 | 52.4 | 42.7 | 1.227 |
| 48 | 66.9 | 49.0 | 1.366 |

-continued

Ethanol as carbon source

| Time (hr) | AFP (mg/kg fermentation broth) | Dry matter (g/kg) | Specific production* (mg/g) |
|---|---|---|---|
| 51 | 78.7 | 55.0 | 1.432 |
| 54 | 93.7 | 60.6 | 1.546 |
| 57 | 112.2 | 64.8 | 1.732 |
| 60 | 132.1 | 68.6 | 1.925 |
| 63 | 151.2 | 71.9 | 2.104 |
| 66 | 165.8 | 75.5 | 2.195 |

*Specific production: mg AFP/g dry matter

On the basis of these results it is concluded that production of AFP when in the feed phase after limiting conditions, arise, the feeding with medium containing a carbon source which is 100 wt % ethanol is continued, leads to surprisingly high specific production of AFP.

It was observed that the biomass production was constant without loss of absolute AFP productivity.

Comparative Example

Growth medium in feed phase did not contain ethanol but 100 wt % glucose as carbon source. The medium for this experiment is described above. Also the fermenter feed conditions are specified above with the following exceptions:

The feed medium was applied to the fermenter from one feed bottle, containing all components and was fed to the fermenter through the bottom plate. An exponential feed rate was applied according to eq 1.

Feed parameters were according to table 3 with exception for the X0-value which was set to 2.11 mol to result in the same feed rate with one feed bottle as in the ethanol fermentation with two feed bottles on one pump.

The results were as follows:

| Time (hr) | AFP (mg/kg) | Dry matter (g/kg) | Specific production* (mg/g) |
|---|---|---|---|
| 0 | 0 | 1.9 | 0 |
| 3 | 0 | 3.3 | 0 |
| 6 | 0 | 5.5 | 0 |
| 9 | 0 | 7.2 | 0 |
| 12 | 0 | 10.4 | 0 |
| 15 | 0 | 11.4 | 0 |
| 18 | 0 | 13.3 | 0 |
| 21 | 0.8 | 15.8 | 0.049 |
| 24 | 2.6 | 18.4 | 0.142 |
| 27 | 5.8 | 20.3 | 0.286 |
| 30 | 10.3 | 24.6 | 0.421 |
| 33 | 16.8 | 28.6 | 0.588 |
| 36 | 25.5 | 33.0 | 0.773 |
| 39 | 35.4 | 37.5 | 0.942 |
| 42 | 46.8 | 43.4 | 1.077 |
| 45 | 60.3 | 50.0 | 1.204 |
| 48 | 74.4 | 55.9 | 1.331 |
| 51 | 90.8 | 62.9 | 1.445 |
| 57 | 126.4 | 79.2 | 1.596 |
| 60 | 135.2 | 79.5 | 1.701 |
| 63 | 135.13 | 79.3 | 1.705 |

It is concluded that when the growth medium contains only glucose as the carbon substrate, AFP production is decreased up from the moment when limiting conditions set in. AFP production no longer increases and the production declines.

Results

Example 2

| Ethanol as carbon source | | | Glucose as carbon source (comparative example 2) | | |
|---|---|---|---|---|---|
| VHH (mg/kg fermentation broth) | Dry matter (g/kg) | Specific production* (mg/g) | VHH (mg/kg fermentation broth) | Dry matter (g/kg) | Specific production* (mg/g) |
| 0 | 0.91 | 0 | 0 | 6.63 | 0.00 |
| 0 | 6.17 | 0 | 0 | 12.34 | 0.00 |
| 0 | 11.66 | 0 | 106.33 | 25.60 | 4.15 |
| 141.77 | 21.26 | 6.67 | 248.09 | 35.65 | 6.96 |
| 927.40 | 48.68 | 19.05 | 425.30 | 45.02 | 9.45 |
| 1063.26 | 51.65 | 20.58 | 673.40 | 57.59 | 11.69 |
| 1222.75 | 56.68 | 21.57 | 856.52 | 72.22 | 11.86 |
| 1151.87 | 55.31 | 20.83 | 915.59 | 71.31 | 12.84 |

*Specific production: mg heterologous protein/g dry matter

It is concluded that the specific production of heterologous protein using ethanol as carbon source is much higher than on glucose as carbon source.

Results

Example 3

| Ethanol as carbon source | | | | Glucose as carbon source (comparative example 3) | | | |
|---|---|---|---|---|---|---|---|
| Time (h) | VHH (mg/kg fermentation broth) | Dry matter (g/kg) | Specific production* (mg/g) | Time (h) | VHH (mg/kg fermentation broth) | Dry matter (g/kg) | Specific production* (mg/g) |
| 3 | 0 | 2.87 | 0 | 21 | 103.45 | 17.19 | 6.02 |
| 6 | 0 | 5.73 | 0 | 27 | 127.59 | 20.78 | 6.14 |
| 9 | 0 | 6.93 | 0 | 33 | 227.59 | 28.66 | 7.94 |
| 33 | 268.97 | 45.37 | 5.93 | 39 | 272.41 | 36.78 | 7.41 |
| 36 | 417.24 | 50.86 | 8.20 | 45 | 327.59 | 47.52 | 6.89 |
| 39 | 537.93 | 54.45 | 9.88 | 51 | 413.79 | 57.07 | 7.25 |
| 42 | 689.66 | 56.36 | 12.24 | 57 | 503.45 | 64.48 | 7.81 |
| | | | | 63 | 565.52 | 67.10 | 8.43 |
| | | | | 69 | 596.55 | 69.73 | 8.56 |

*Specific production: mg heterologous protein/g dry matter

It is concluded that the specific production of heterologous protein using ethanol as carbon source is much higher than on glucose as carbon source.

Results

Example 4

| Ethanol as carbon source | | | | Glucose as carbon source (comparative example 4) | | | |
|---|---|---|---|---|---|---|---|
| Time (h) | VHH (mg/kg fermentation broth) | Dry matter (g/kg) | Specific production* (mg/g) | Time (h) | VHH (mg/kg fermentation broth) | Dry matter (g/kg) | Specific production* (mg/g) |
| 0 | 0.00 | 0.72 | 0.00 | 15 | 13.79 | 10.51 | 1.31 |
| 12 | 0.00 | 9.79 | 0.00 | 21 | 27.59 | 16.00 | 1.72 |
| 18 | 13.79 | 17.19 | 0.80 | 27 | 55.17 | 19.10 | 2.89 |
| 24 | 155.17 | 25.31 | 6.13 | 33 | 117.24 | 25.07 | 4.68 |
| 30 | 275.86 | 35.82 | 7.70 | 39 | 155.17 | 32.00 | 4.85 |
| 36 | 403.45 | 46.80 | 8.62 | 45 | 213.79 | 45.13 | 4.74 |
| 39 | 472.41 | 50.63 | 9.33 | 51 | 210.34 | 56.83 | 3.70 |
| 42 | 620.69 | 53.49 | 11.60 | 57 | 255.17 | 68.30 | 3.74 |
| 45 | 675.86 | 58.03 | 11.65 | | | | |

*Specific production: mg protein/g dry matter

It is concluded that the specific production of heterologous protein using ethanol as carbon source is much higher than on glucose as carbon source.

The invention claimed is:

1. A method for the production of a heterologous protein by a fungus which method comprises a batch phase, an induction phase and a feed phase, said batch phase comprising growing fungal cells to a cell density of at least 5/gl on a batch medium comprising any carbon source, without specific preference; and said induction phase and feed phase comprising:
    (a) subsequently growing the fungal cells to a cell density of from 10 to 90 g/l, using a feed medium comprising an inducer and a carbon source wherein 50-100 wt. % of said carbon source is ethanol; then
    (b) creating limiting growth conditions by a method selected from the group comprising reducing the oxygen concentration in the fermenter medium to from 0 to below 30%; overfeeding the medium with ethanol until the ethanol level in the medium is at or above the growth limiting concentration for the cells of the strain that is grown in the medium; or decreasing the level of other essential ingredients for growth of the cells said ingredients being selected from nitrogen, phosphor, sulfur and vitamins; and then
    (c) further growing the cells on a medium comprising a carbon source wherein 50-100 wt. % of said carbon source is ethanol; with the proviso that the method does not relate to expression methods wherein ethanol is both used as inducer and as the carbon source.

2. The method according to claim 1 wherein the method is carried out in a fermenter, which is fed with feed medium at a feed rate which is such that the ethanol concentration in the fermenter is maintained below 10 vol %.

3. The method according to claim 1 further comprises carrying out the method as a repeated fed batch process.

4. The method according to claim 1 wherein the inducer is selected from the group comprising galactose, methanol, temperature and phosphates.

5. The method according to claim 1, wherein the feed medium comprises from 0.1 to 10 wt % galactose.

6. The method according to claim 1, wherein the carbon source comprises 80-100 wt % ethanol.

7. The method according to claim 1, wherein the fungus is a yeast.

8. The method according to claim 1 wherein the heterologous protein or peptide is selected from antifreeze peptides, antibodies or fragments thereof, and enzymes.

9. The method according to claim 1 wherein the batch medium comprises from 1-40 wt. % glucose, water, trace metals, and wherein the feed medium comprises from 5 to 35 vol. % ethanol, 0.1-10 wt. % galactose, water, trace metals, and optionally antifoaming agent yeast extract, vitamins, phosphate salts and sulphate salts and wherein the "feed rate" "φ" is from 0.25 to 4 g/min on 10 liter scale.

10. The method according to claim 1 wherein the batch medium further comprises an antifoaming agent, yeast extract, vitamins, phosphate salts and sulphate salts.

11. The method according to claim 7 wherein the yeast is *Saccharomyces cerevisiae*.

12. The method according to claim 1 wherein in step (a) the fungal cells are grown to a cell density of from 40 to 90 g/l.

* * * * *